United States Patent [19]
Garrett

[11] Patent Number: 5,826,271
[45] Date of Patent: Oct. 27, 1998

[54] EYEWEAR IN COMBINATION WITH A VISOR

[75] Inventor: LaMills A. Garrett, Columbia, S.C.

[73] Assignee: Vista Visor Inc, Columbus, Ohio

[21] Appl. No.: 818,633

[22] Filed: Mar. 14, 1997

[51] Int. Cl.$^6$ .................................. A42B 1/06; A42B 1/24
[52] U.S. Cl. .......................... 2/10; 2/12; 2/209.13; 2/453; 351/155
[58] Field of Search ............................... 2/10, 12, 13, 9, 2/453, 209.13; 351/155, 158

[56] References Cited

U.S. PATENT DOCUMENTS

| 2,708,270 | 5/1955 | Von Gunten | 2/13 |
| 5,347,655 | 9/1994 | Garrett | 2/10 |
| 5,533,208 | 7/1996 | Tonoyan et al. | 2/453 X |

Primary Examiner—Peter Nerbun
Attorney, Agent, or Firm—Michael A. Mann

[57] ABSTRACT

A sun visor with attached sunglasses rotatable incrementally between an up position, a down position and several intermediate positions. The frame of the sunglasses is equipped with a pair of circular shoulders from which a pair of posts extend perpendicularly therefrom. The visor has a pair of depending members, each having a hole formed therethrough which is surrounded by a circular pattern of domes extending from the inner faces of the members. A pair of ribs extend from each circular shoulder which abut the domes when the posts are placed through the holes. The ribs fit within the interstices defined by adjacent domes and resist rotation of the frame, but do not prevent rotation if sufficient force is applied. The ends of the posts are conical and slotted to facilitate insertion of the posts through the holes in the depending members and prevent removal because the diameter of the base of the cone is larger than the diameter of the hole.

15 Claims, 3 Drawing Sheets

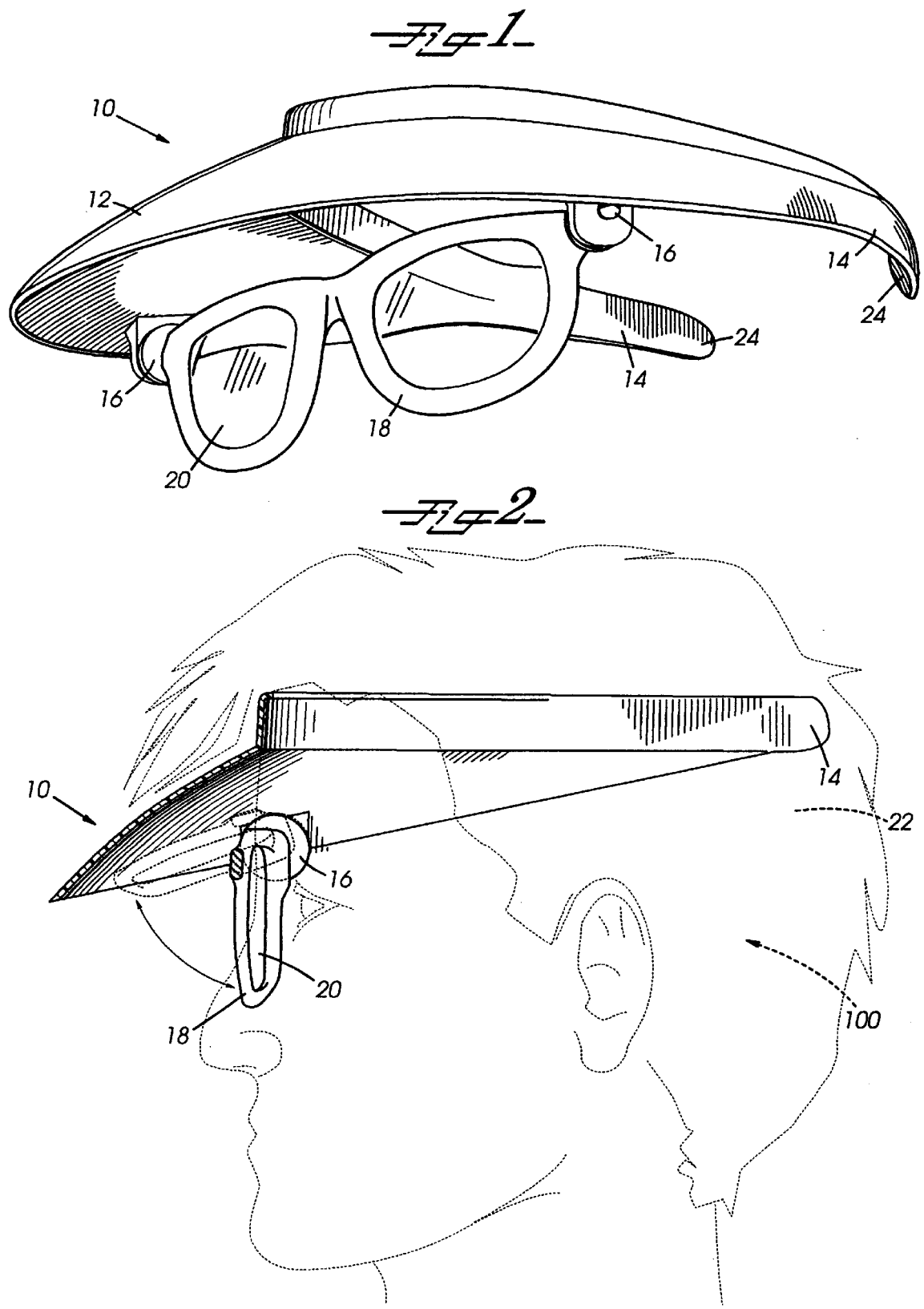

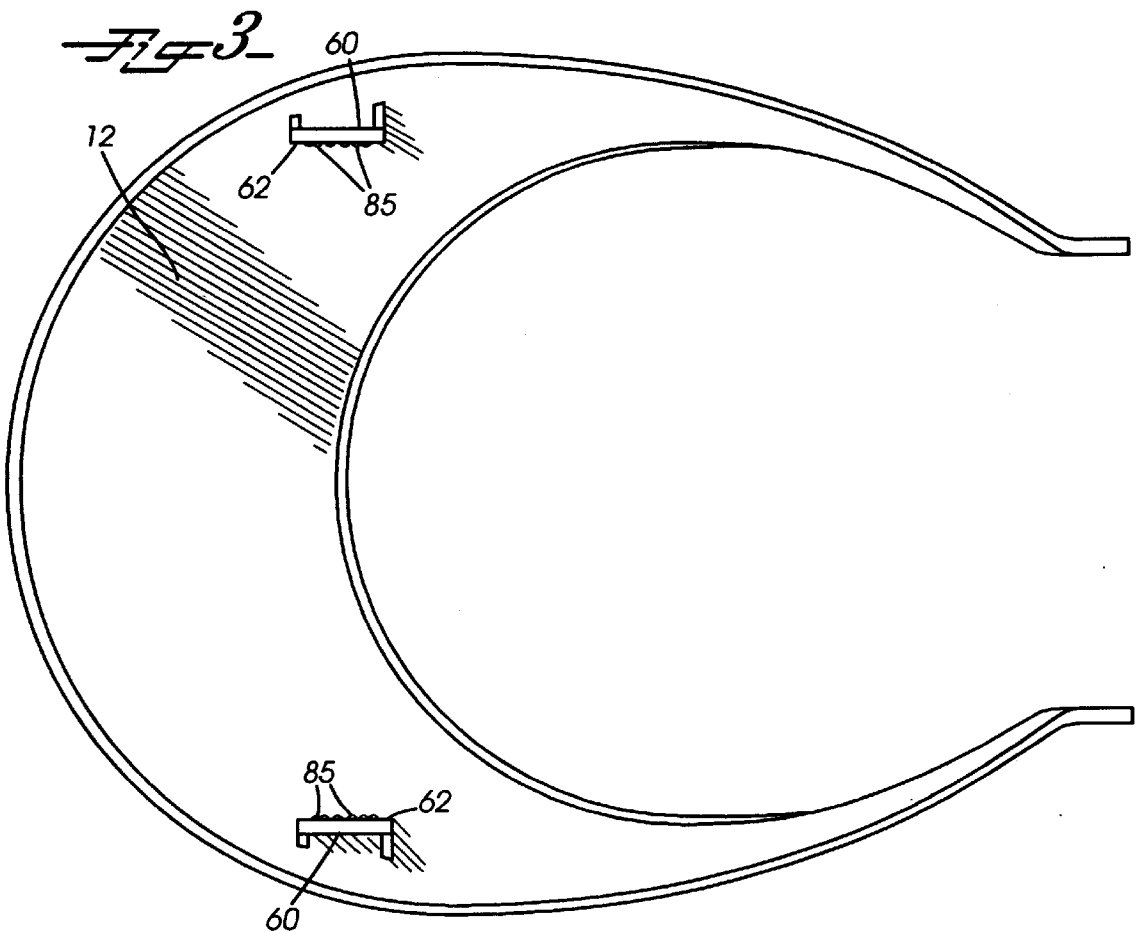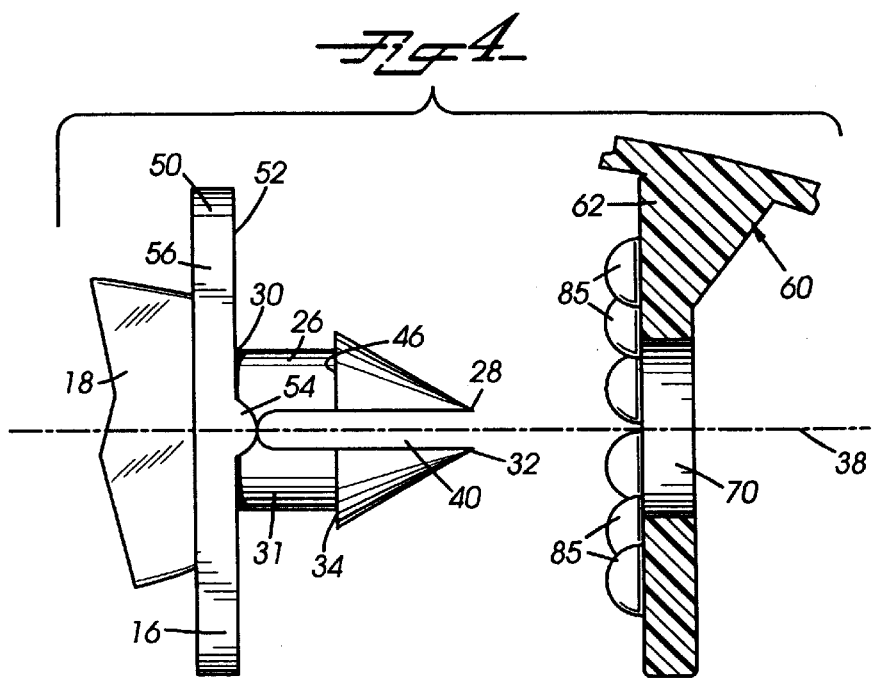

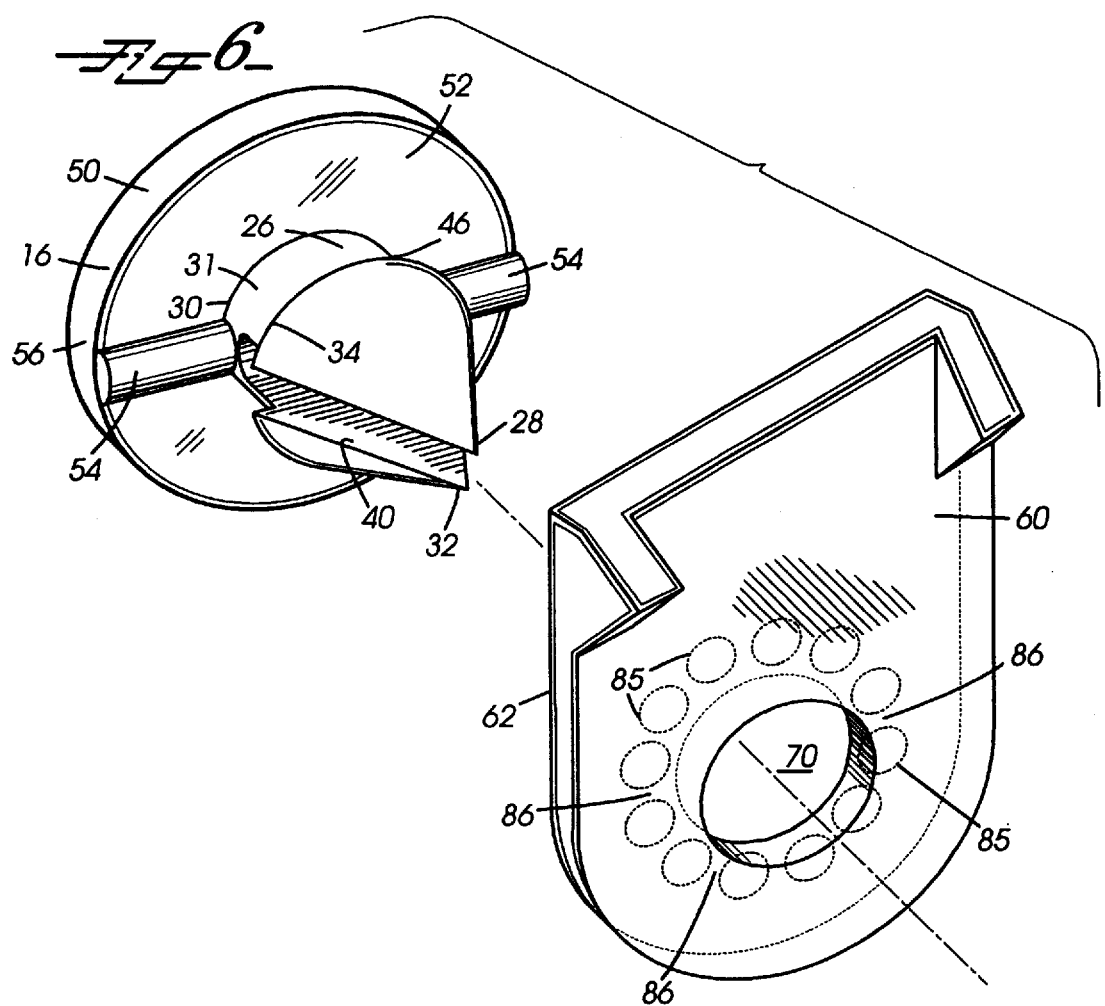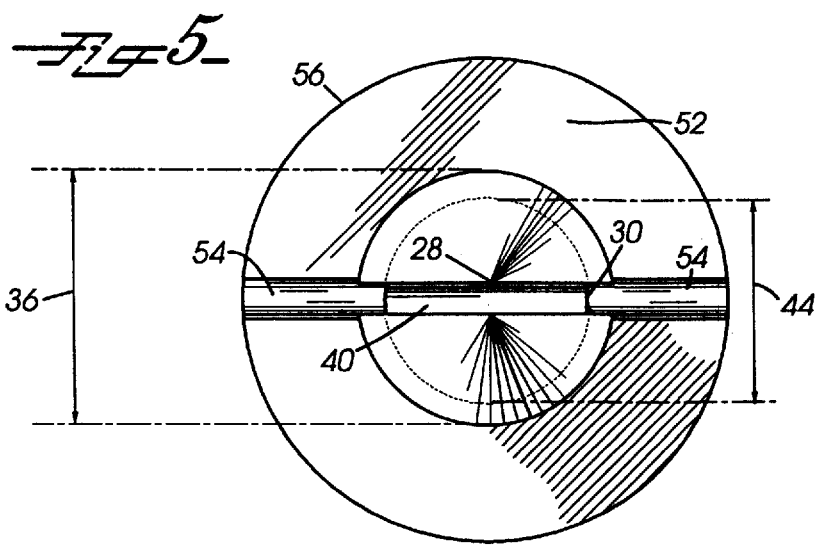

EYEWEAR IN COMBINATION WITH A VISOR

BACKGROUND OF THE INVENTION

1. Field of the Invention

The present invention relates to a device that combines a sun visor with eyewear. More particularly, the present invention relates to a sun visor with a lens having a frame, which can be incrementally rotated about its axis.

2. Discussion of Background

Our society thrives on outdoor activity. Those of us who enjoy the outdoors usually carry eyewear to protect against intense visible light and ultraviolet rays. Sunglasses, visors, or the combination of both have traditionally blocked dangerous ultraviolet sunlight while providing the user with a more comfortable perspective to better enjoy an outdoor activity.

Sunglasses are available in a multitude of styles and sizes, but may not be suited for more active pursuits. Sun visors have many advantages: they are effective sun blocks, durable, inexpensive and often stylish for the consumer, and easy to manufacture. Sun visors, however, have limited shielding against reflecting sunlight, do not block ultraviolet light from the eyes and can be inadequate for glare off the surface of water or snow. Combining sunglasses with a sun visor is perhaps the best practical solution to enjoy the advantages of both worlds.

Sun visors that combine tinted lenses having a frame are well known. U.S. Pat. No. 2,638,593 granted to Eloranta and U.S. Pat. No. 4,815,838 granted to Liautaud attach the eyewear frame and a visor through slits formed in a visor that receive tabs notched on the side of the eyewear. U.S. Pat. No. 5,007,109 granted to Wheeler uses buckles that fit into snaps. U.S. Pat. No. 4,781,451 granted to McAllen uses eyeglass supports with VELCRO® patches that attach to headbands, caps and the like.

The rotation of a lens frame attached to a sun visor between an up and a down position is certainly advantageous for storing or giving alternate choices of protection for blocking more or less intense light. Combinations of visors with lenses having a frame that feature incremental rotation are well known. U.S. Pat. No. 1,696,198 granted to Gross and U.S. Pat. No. 5,105,475 granted to Lynd, et al. teach of incrementally rotating the eyeglasses on a visor or cap.

Although visors with eyewear exist, there remains a need for designs that permit incremental rotation of lenses from a stored, non-operational position to an operational position.

SUMMARY OF THE INVENTION

According to its major aspects and broadly stated, the present invention is a sun visor combined with a lens that has a frame, which can be incrementally rotated about an axis from a stored or "up" position against the visor to one or more "down" or operational positions. The device is worn on a user's head to protect from sunlight. The device comprises a visor, means for holding the visor to the head, a frame, one or more lenses secured to the frame, and means for securing the frame to the visor. The visor is a typical visor in its preferred embodiment, that is, a member that extends from the forehead forward to shield the eyes from overhead sunlight and may slope slightly downward from the forehead. The visor is secured to the head by a pair of arms that resiliently engage the sides of the head and are attached to the frame, or, alternatively, a head-encircling strap or elastic band. The present visor has two spaced-apart, depending members each of which contains a hole dimensioned to receive part of the frame that will secure the frame to the visor. Surrounding each hole are a plurality of hemispherical or dome-like projections from the depending members, with each "dome" separated by the same distance from the two adjacent domes. The domes are equidistant from and arranged in a circular pattern about the hole.

The securing means comprises a pair of posts on opposing sides of the frame, each post having a first end and a second end. The first end passes through the holes in the depending members of the visor and is preferably conical in shape to facilitate insertion. The second end of the securing means is cylindrical in shape and is attached to a circular shoulder, extending radially with respect to the central axis of the post. Each shoulder is formed with a pair of ribs that are raised above the surface of the shoulders in the direction of the post. Each rib begins at the perimeter of the circular shoulder and terminates at the point of contact with the exterior surface of the post.

An important feature of the present invention is the combination of the domes surrounding the hole and the ribs formed in the shoulders of the securing means. The ribs are dimensioned to fit securely in the interstices defined by two adjacent domes, thereby maintaining the frame in a desired position. Moreover, the shape of both the domes and the ribs permits the incremental rotation of the frame, which enables the user to precisely adjust the position of the frames, simply and effectively.

The conical first end of the post is another feature of the present invention. The cone is preferably slit and the base of the cone defines a shoulder. The conical first end is easily pushed through the visor hole as the two halves of the cone, one on either side of the slit are compressed together by the force exerted on the cone by the edge of the hole in the visor, but once through the hole past the base of the cone, the two halves spring resiliently apart, and the shoulder prevents removal of the frame from the visor.

Other features and advantages will be apparent to those skilled in the art from a careful reading of the Detailed Description of a Preferred Embodiment presented below and accompanied by the drawings.

BRIEF DESCRIPTION OF THE DRAWINGS

In the drawings,

FIG. 1 is a perspective view of the device according to a preferred embodiment of the present invention;

FIG. 2 is a cross sectional view of the device according to a preferred embodiment of the present invention with a person illustrated in ghost;

FIG. 3 is a bottom view of a visor showing the depending members according to a preferred embodiment of the present invention;

FIG. 4 is a partial cross sectional side view of a post and depending member according to a preferred embodiment of the present invention;

FIG. 5 is a front view of a post according to a preferred embodiment of the present invention; and FIG. 6 is an exploded view of a post and depending member according to a preferred embodiment of the present invention.

DETAILED DESCRIPTION OF A PREFERRED EMBODIMENT

The present invention is a device that combines eyewear with a visor adapted to be worn about the head. Referring now to FIGS. 1 and 2, there is shown a perspective view and a side cross sectional view, respectively, of a device according to a preferred embodiment of the present invention and generally indicated by reference numeral 10. Device 10 comprises a visor 12, holding means 14 for holding visor 12 to the head 22 of a user, a frame 18, a pair of lenses 20 secured to frame 18, and securing means 16 for securing frame 18 to visor 12.

Visor 12 is a generally arcuate cantilever, preferably formed from styrene-based composition by injection molding. Visor 12 rests against the brow of a user 100 and extends outward and slightly downward so as to shield the eyes from direct sunlight overhead or in the foreground. Holding means 14 engages head 22 of user 100 to hold visor 12 in position. As illustrated, holding means 14 comprises a pair of arms 24, however, it will be recognized by those with ordinary skill in the art that holding means 14 may embody a pair of interlocking straps, a continuous elastic band, or a cap, without departing from the spirit and scope of the present invention.

Securing means 16 is located on opposing sides of frame 18, and preferably formed integral therewith, for securing frame 18 to visor 12 in such a way that frame 18 can incrementally rotate from an up position, engaging visor 12, to a down position for use, or one of a number of positions therebetween, as illustrated in FIG. 2. In any of these positions: up, down, or intermediate, the angle between visor 12 and frame 18 is not likely to change unless a modest force is applied to frame 18.

Referring now to FIGS. 3 through 6, securing means 16 comprises a pair of posts 26 on each end of frame 18, directed laterally. Each post 26 has a first end 28 and a second end 30. First end 28 is conical in shape, that is, first end 28 has a tip 32, a base 34, a diameter 36, and an axis 38 perpendicular to diameter 36 and extending through tip 32 and base 34. First end 28 of post 26 has a slot 40 formed therein, beginning at tip 32 and extending along axis 38 through base 34. Attached to second end 30 of post 26 is circular shoulder 50. Circular shoulder 50 is positioned perpendicular to axis 38 of post 26.

Second end 30 of post 26 is cylindrical in shape and has a diameter 44. As illustrated in FIGS. 4 and 5, diameter 36 at base 34 of first end 28 is greater than diameter 44 of second end 30 of post 26 thereby defining a shoulder 46. Face 52 of shoulder 50 is formed with a pair of ribs 54 having an arcuate shape. Ribs 54 extend in the direction of post 26, beginning at perimeter 56 of shoulder 50 and terminating at exterior surface 31 of end 30 of post 26.

Visor 12 has two spaced-apart, earlobe-like, depending members 60. Each member 60 is formed with a hole 70 dimensioned to receive one post 26. Each member 60 has an inner face 62. Each inner face 62 has extending therefrom a plurality of domes 85. As illustrated in FIG. 5, domes 85 surround hole 70 in a circular pattern. Each dome 85 is equidistant from the two adjacent domes 85. In addition, there is an equal distance between the center of hole 70 and each dome 85. Adjacent domes 85 define interstices 86.

Depending members 60 are constructed of a resilient material such as plastic; frame 18 may also be made of plastic but not necessarily a resilient plastic. First end 28 of post 26 is configured to fit through one hole 70 of each member 60. The resilient material of depending member 60 deforms under the influence of the forces of first end 28 of post 26 being pushed through hole 70. Movement of first end 28 through hole 70 is simplified by slot 50 which enables the diameter of first end 28 to momentarily decrease as a result of force exerted by the edge of hole 70. When diameter 36 of base 34 of first end 28 is through hole 70, shoulder 46 thereafter impedes the removal of post 26 from member 60. Hole 70 has a diameter slightly larger than diameter 44 of second end 30 of post 26, and thus, second end 30 fits securely therein. When post 26 has been inserted through hole 70, shoulder 50 will abut domes 85 with ribs 54 positioned between adjacent domes 85, within interstices 86.

Depending member 60 grips second end 30 of post 26. The small gap between diameter 44 and the diameter of hole 70 permits the rotation of frame 18 between the up and down positions and all intermediate positions. Dome 85 resists rotation of post 26 when ribs 54 are positioned within interstices 86. As frame 18 is rotated, the force required to rotate alternately increases and then decreases as each rib 54 is moved over the outer surface of a dome 85 and into an interstice 86. Therefore, post 26 will remain in one of "preferred" positions, i.e. when ribs 54 are between two adjacent domes 85, unless force is supplied to move ribs 54 over domes 85. Incremental rotation is important between a vertical position in front of the eyes of the user and a horizontal position away from the eyes of the user and against the inner side of visor 12 for adjusting the angle between visor 12 and frame 18 to suit the preference of user 100 and, in the up position, to store frame 18.

It will be apparent to those skilled in the art from a careful reading of the detailed description of the foregoing preferred embodiment that many modifications and substitutions can be made in the foregoing without departing from the spirit and scope of the invention as defined by the appended claims.

What is claimed is:

1. A device for use on the head of a user, comprising:
   a visor having two depending members, each depending member having a hole formed therein, said hole having a diameter, each member having an inner face, said inner face having a plurality of domes extending therefrom, said plurality of domes surrounding said hole;
   means for holding said visor to the head of the user;
   a frame;
   a lens secured to said frame; and
   means for securing said frame to said visor so that said frame has an up position against said visor and a down position away from said visor, said frame rotatable between said up and said down positions, said securing means having two posts, each post of said two posts having a first end and a second end, said second end of said each post being attached to a circular shoulder positioned perpendicularly to said each post, said shoulder having an inner face, said shoulder having a pair of ribs extending from a perimeter of said shoulder toward said post, said ribs abutting said domes, said ribs of said shoulder and said domes permitting incremental rotation of said post.

2. The device as recited in claim 1, wherein said holding means further comprises a pair of arms, said pair of arms engaging the head of the user to hold said visor thereon.

3. The device as recited in claim 1, wherein said domes are arranged in a circular pattern around said hole, wherein said domes define interstices therebetween, and wherein said ribs fit in said interstices.

4. The device as recited in claim 1, wherein said first end of said each post has a conical shape and wherein said second end of said post has a cylindrical shape.

5. The device as recited in claim 1, wherein said first end of said each post has a conical shape, wherein said conical shape has a tip and a base, wherein said base has a diameter, wherein said second end has a cylindrical shape, said cylindrical shape having a diameter, and wherein said diameter of said cylindrical shape of said second end of said post is less than said diameter of said base.

6. A device for use on a head of a user, comprising:

a visor having two members depending therefrom, each member having a hole formed therein, said hole having a diameter;

means for holding said visor to said head;

a frame;

a lens secured to said frame;

a pair of posts on said frame for securing said frame to said visor so that said frame has an up position against said visor, a down position away from said visor, and an intermediate position between said up and down positions, said frame rotatable between said up and said down positions, each post of said pair of posts having a first end and a second end, said second end of said each post being attached to a circular shoulder positioned perpendicularly to said each post, said shoulder having an inner face, said shoulder having a pair of ribs extending from a perimeter of said shoulder toward said post; and means formed in said visor for resisting rotation of said frame from said up position, said down position and said intermediate position.

7. The device as recited in claim 6, wherein each member of said members has an inner face, and wherein said resisting means further comprises a plurality of domes extending from said inner face of said each member of said members, said domes surrounding said hole in a circular pattern.

8. The device as recited in claim 6, wherein said holding means further comprises a pair of arms, said pair of arms engaging the head of the user to hold said visor thereon.

9. The device as recited in claim 6, wherein said first end of said each post has a conical shape and wherein said second end of said post has a cylindrical shape.

10. The device as recited in claim 6, wherein said first end of said each post has a conical shape, wherein said conical shape has a tip and a base, wherein said base has a diameter, wherein said second end has a cylindrical shape, said cylindrical shape having a diameter, and wherein said diameter of said cylindrical shape of said second end of said post is less than said diameter of said base.

11. The device as recited in claim 6, wherein said first end of said each post has a conical shape, wherein said second end of said post has a cylindrical shape and wherein said each post of said posts has a slot running axially therethrough.

12. A device for use on the head of a user, comprising:

a visor having two depending members, each depending member having a hole formed therein, said hole having a diameter, each member having an inner face, said inner face having a plurality of domes extending therefrom, said plurality of domes surrounding said hole;

means for holding said visor to the head of the user;

a frame;

a lens secured to said frame; and means for securing said frame to said visor so that said frame has an up position against said visor and a down position away from said visor, said frame rotatable between said up and said down positions, said securing means having two posts, each post of said two posts having a first end and a second end, said second end of said each post being attached to a circular shoulder positioned perpendicularly to said each post, said shoulder having an inner face, said shoulder having a pair of ribs extending from a perimeter of said shoulder toward said post, said ribs abutting said domes, said first end of said each post having a conical shape, said second end of said each post having a cylindrical shape, said each post having a slot running axially therethrough, said ribs of said shoulder and said domes permitting incremental rotation of said post.

13. The device as recited in claim 12, wherein said holding means further comprises a pair of arms, said pair of arms engaging the head of the user to hold said visor thereon.

14. The device as recited in claim 12, wherein said first end of said each post has a conical shape and said second end of said post has a cylindrical shape.

15. The device as recited in claim 12, wherein said first end of said each post has a conical shape, wherein said conical shape has a tip and a base, wherein said base has a diameter, wherein said second end has a cylindrical shape, said cylindrical shape having a diameter and wherein said diameter of said cylindrical shape is less than said diameter of said base.

* * * * *